United States Patent [19]

Voo et al.

[11] Patent Number: 5,464,850
[45] Date of Patent: Nov. 7, 1995

[54] SYNERGISTIC PRESERVATIVE SYSTEMS FOR CHEMISTRY REAGENTS

[75] Inventors: Liann Voo, West Roxbury; Dennis C. Tagliaferro, Tewksbury; Joan B. Wilson, Walpole, all of Mass.

[73] Assignee: Ciba Corning Diagnostics Corp., Medfield, Mass.

[21] Appl. No.: 245,303

[22] Filed: May 17, 1994

Related U.S. Application Data

[63] Continuation of Ser. No. 771,704, Oct. 4, 1991, abandoned.

[51] Int. Cl.$^6$ ............................................. A61K 31/425
[52] U.S. Cl. ........................................ 514/372; 514/389
[58] Field of Search ........................... 514/372, 389

[56] References Cited

U.S. PATENT DOCUMENTS

| | | | |
|---|---|---|---|
| 4,844,891 | 7/1989 | Rosen et al. | 424/76.4 |
| 4,906,651 | 3/1990 | Hsu | 514/372 |
| 4,964,892 | 10/1990 | Hsu | 71/67 |

FOREIGN PATENT DOCUMENTS

| | | | |
|---|---|---|---|
| 0375367 | 6/1990 | European Pat. Off. | A01N 43/80 |
| 7054104 | 3/1982 | Japan | A01N 43/80 |
| 9212406 | 12/1984 | Japan | A01N 43/80 |

OTHER PUBLICATIONS

Kabara, Jon J., Cosmetic and Drug Preservation, 1984, Marcal Dekker, Inc., N.Y., pp. 129–141, 165–190.
DeKrujp et al 108 CA: 156233N 1988.
Zeelie et al 100 CA: 108960K 1984.

*Primary Examiner*—Russell Travers
*Attorney, Agent, or Firm*—Arthur S. Morgenstern; Nicholas I. Slepchuk, Jr.; Judith A. Roesler

[57] ABSTRACT

A family of solutions that can be used to calibrate one or more electrochemical sensors has been developed. These systems can be used to determine analytes in biological fluids, such as whole blood, serum, plasma and urine. Since these reagents require preservatives in order to make their shelf life and use life commercially feasible, a system of preservatives which exhibits unexpected synergy in antimicrobial capabilities has been identified. The preferred preservative system includes a mixture of 5-chloro-2-methyl-4-isothiazolin-3-one; 2-methyl-4-isothiazolin-3-one; and 1,3-bis-(hydroxymethyl)-5,5-dimethyl-2,4-imidazolidinedione.

9 Claims, No Drawings

SYNERGISTIC PRESERVATIVE SYSTEMS FOR CHEMISTRY REAGENTS

This is a continuation of application Ser. No. 07/771,704 filed on Oct. 4, 1991, now abandoned.

BACKGROUND OF THE INVENTION

Clinical laboratory instruments are utilized by hospitals, clinical laboratories, doctors' offices and the like for analyzing body fluids, such as whole blood, serum or plasma, in order to diagnose diseases. Since the chemistries are somewhat similar for related areas, such as the veterinary diagnostic area and the analysis of food components, these instruments have a broader usefulness, but, by far, their largest market is in the human clinical chemistry area. In order to utilize these instruments, a broad range of reagents are necessary. First, there are control materials (or reference materials) which are used to confirm that the instrument is working properly. These are similar to the materials that are being analyzed, usually of known composition and analyzed in a manner similar to the way specimens are analyzed. Second, there are calibrators, which are used to calibrate the system, i.e., used to draw a calibration curve for the analyte. Third, there are chemicals, such as wash solutions, deproteinizing reagents, conditioning reagents, buffers, diluents, precipitants, active ingredients, and other materials which are used to prepare the specimen samples. Additional reagents or systems may also be needed for the instruments to operate.

The sensors used in these instruments can be based on a variety of chemical principles, for example they may rely on spectrophotometry, potentiometry, amperometry, etc. Many, but not all, of the reagents are water based. Others may be lyophilized or powder reagents and may need to be reconstituted with water before use. Still others may be solvent based or in other forms. Because these reagents contain nutrients for microorganisms, microbial growth is frequently a problem, especially for commercially distributed products, which often require months or years of shelf life in order to be commercially practical products.

One subcategory of such instruments and chemicals are those which are used in the critical care area, where the analytical results must be obtained quickly, for example, when the patient is in the operating room or emergency room. These are used to measure such items as the concentration in the blood of such components as carbon dioxide, oxygen, total hemoglobin, sodium, potassium, chloride, calcium, lactate or glucose, and such physical properties as pH. In this environment it is especially important that the systems work properly, because of the need for personnel to quickly make decisions regarding diagnosis and treatment of the patient. This means that, among other things, the reagents must not become spoiled because of the action of microorganisms, and, therefore, it is customary to use microbicides (also called antimicrobial agents and preservatives) in these systems.

SUMMARY OF THE INVENTION

A family of solutions that can be used to calibrate one or more electrochemical sensors has been developed. These systems can be used to determine analytes in biological fluids, such as whole blood, serum, plasma and urine. Since these reagents require preservatives in order to make their shelf life and use life commercially feasible, a system of preservatives which exhibits unexpected synergy in antimicrobial capabilities has been identified. The preferred preservative system includes a mixture of 5-chloro-2-methyl-4-isothiazolin-3-one; 2-methyl-4-isothiazolin-3-one; and 1,3-bis-(hydroxymethyl)-5,5-dimethyl-2,4-imidazolidinedione.

DETAILED DESCRIPTION OF THE INVENTION

In determining the antimicrobial system to use for critical care products, numerous factors had to be considered. Although there are many microbicides available, these antimicrobial products must be carefully screened, because they are not equally effective against the variety of microorganisms that can grow in these products. Furthermore, care must be taken to assure that the antimicrobials are not antagonistic to each other, will not interfere with the usefulness of the reagent it is used in (for example, interfere with the active ingredients in the product), nor interfere with any component of any other reagent it comes in contact with, nor will they migrate into the packaging materials they are stored in and thus not be available to preserve the chemical system, nor affect the performance of the instrument or its sensors, nor interfere with any other aspect of the system. In addition, the antimicrobial agent(s) must be stable and effective for the shelf life of the product it is used in, both in original form of the reagent and, if applicable, in reconstituted form. Furthermore, the antimicrobial must maintain effectiveness and stability in all forseeable environments, such as temperature and level of light, to which the reagent and its in-use concentration may be exposed. If there are any degradation products that result from use of the antimicrobial, these must be innocuous to the system.

The sorts of microorganisms frequently encountered in the reagents include those that are water-borne or air-borne. The genera include Staphylococcus, Streptococcus, Pseudomonas, Proteus and others. In addition, various molds, yeasts and other microorganisms may infect the systems. These microbes may also arise from contaminated raw materials, from equipment the product is compounded in, from contact with the instrument, from contact with the specimen and other sources. Thus, to be truly effective, the antimicrobials must not merely inhibit the growth of microorganisms, but also must destroy any microorganisms which are introduced by any of the aforementioned factors and which interfere with the analysis.

Aside from efficacy, selection of microbicides is also affected by safety, environmental and regulatory factors. For example, worker safety in handling the pure microbicide should be considered, as should safety to the laboratory technician in using the reagent. Disposal of certain materials is regulated by appropriate government agencies, as is registration and permissible usage level of the microbicide, and the selected microbicides must be acceptable from these aspects also.

Decomposition caused by the microbes can cause detrimental effects, in part because of the acidic products which are formed. In particular, these can change the pH of the calibrator. Since pH of the specimen itself is one important factor in the critical care area, it is important that the microbicide used works quickly to prevent the system from being overrun by microorganisms, which can cause miscalibration of the instrument. Furthermore, because of the design of the instruments, there are certain areas in which the solutions can remain stagnant, thus potentially encouraging microbial growth and affecting pH, as mentioned above, which can potentially affect performance of the electrodes. In addition, microbial growth in the sensors can affect pO$_2$ (oxygen partial pressure) of the samples during measurement.

In our evaluation of preservatives, we have used, therefore, a 24-hour kill time as a measure of antimicrobial effectiveness. In addition, we have used tight control limits on the product specifications to assure that the preservative system does not detrimentally affect product performance. The allowable tolerances were as follows:

|      |            |
|------|------------|
| pH ± | 0.003      |
| Na ± | 0.8 mmol/l |
| K ±  | 0.05 mmol/l |
| Cl ± | 1.0 mmol/l |
| Ca ± | 0.02 mmol/l |

The system used to exemplify the product most easily affected by microorganisms was a product which was near neutral pH (pH 7.3 at 37° C.). Various preservatives were added to this system to determine their effectiveness against various microorganisms. It is important to test for microbial efficacy using field isolates along with ATCC (American Type Culture Collection) stock cultures, since the field isolates are in general much more robust and adaptive. The tested organisms included molds (Aspergillus and Penicillium sp.), isolated from spoiled reagents and referred to as KMO ("Kathon Mold Organism") and DMO ("Dantogard Mold Organism"); one or more Pseudomonas organisms found to contaminate the unpreserved system and found to be resistant to Dantogard (a commercial preservative described more fully below), hereafter referred to as "Dantogard Resistant Organism" (DRO); an organism in the Pseudomonas genus found to be a contaminant in the unpreserved system and found to be tolerant to Kathon CG (further described below), i.e., grows at low levels of Kathon CG but is susceptible to higher concentrations, hereafter referred to as "Kathon Tolerant Organism" (KTO); an organism tolerant to Bronidox (further described below), likely Pseudomonas aeruginosa, hereafter referred to as Bronidox Tolerant Organism (BTO); and others. All microorganisms were maintained and all tests were performed using standard procedures known to microbiologists, namely procedures endorsed by the U.S. Pharmacopea and the ATCC.

A large number of preservative systems were evaluated to determine their efficacy in the formulations used in the various reagents. These include the following preservatives:

Kathon CG (Kathon is a registered trademark of the Rohm and Haas Company), which is actually a mixture of 5-choro-2 -methyl-4-isothiazolin-3-one (also named 5-chloro-2-methyl-3(2H)-isothiazolone and methylchloroisothiazolone and chloromethylisothiazolinone) (CAS No. 26172-55-4) and 2 -methyl-4-isothiazolin-3-one (also named 2,methyl-3(2H)-isothiazolone and methylisothiazolone and methylisothiazolinone) (CAS No. 2682-20-4).

Dantogard (a registered trademark of Glyco, Inc.), which is 1,3-bis-(hydroxymethyl)-5,5-dimethyl-2,4-imidazolidinedione (also named 1,3-dihydroxymethyl-5,5-dimethylhydantoin and DMDMH) (CAS No. 6440-58-0).

Bronidox (a registered trademark of Henkel), which is 5 -bromo-5-nitro-1,3-dioxane (CAS No. 30007-47-7).

Kathon LM, which is 2-n-octyl-4-isothiazolin-3-one (CAS No. 26530-20-1).

Oxaban E (a registered trademark of Angus Chemical Co.), which is 1-aza-3,7-dioxa-5-ethylbicyclo(3.3.0)octane, also known as 7-ethylbicyclooxazolidine (CAS No. 7747-35-5).

Kathon CG/II, which contains the same active ingredients as Kathon CG, but in a different matrix of stabilizers.

Proxel (a registered trademark of Imperial Chemical Industries PLC), which is 1,2-benzisothiazolin-3-one (CAS No. 2634-33-5).

The possible synergy in the preservative system was investigated using methods described by Kull, F. C., Eisman, P. C., Sylwestrowicz, H. D. and Mayer, R. L. in Applied Microbiology 9:538–541 (1961), as reported in U.S. Pat. No. 4,906,651. Minimum biocidal concentration (MBC) at 24 hours was determined as the end point of microbial activity. MBC for Kathon CG alone, for Dantogard alone and for various mixtures of Kathon CG and Dantogard were determined and analyzed using the following equation:

$$(Qa/QA)+(Qb/QB)=\text{Synergy Index } (SI)$$

wherein

QA=concentration of compound A in parts per million acting alone, which produced an end point, Qa=concentration of compound A in the mixture which produced an end point, QB=concentration of compound B acting alone which produced an end point, Qb=concentration of compound B in the mixture which produced an end point.

When the sum of (Qa/QA) and (Qb/QB) is greater than one, antagonism is indicated. When the sum is equal to one, additivity is indicated. When the sum is less than one, synergy is demonstrated.

In using only Kathon CG as the preservative in our test system, it was necessary to use it at a concentration of 90 ppm a.i. (active ingredient) to completely kill all the microorganisms in the 24-hour test interval. In using Dantogard alone, it was found that 1600 ppm was needed to kill all the microorganisms. When a mixture of both Kathon and Dantogard were used as the preservative system, it was unexpectedly found that a lower concentration of each was needed.

Using the Kull analysis, it was found that an SI between 0.06 and 0.28 was obtained using various combinations of Kathon CG and Dantogard, showing that high levels of synergy were obtained.

Between 10 and 2400 ppm of Dantogard (concentration at final usage concentration) could be used along with between 1 and 80 ppm of Kathon CG to obtain a preservative system exhibiting synergy. Preferably between 50 and 2200 ppm of Dantogard should be used along with 2 to 60 ppm of Kathon CG. Most preferably between 75 and 2000 ppm of Dantogard should be used along with between 5 and 50 ppm of Kathon CG.

It should be noted that, in the preferred embodiments, the products are formulated using their "in-use" concentrations (i.e., they are used "as is"). However, those knowledgeable in the art would realize that it would also be possible to prepare equivalent reagents having a much higher concentration of preservatives or other ingredients, or both preservatives and other ingredients, which are diluted by the user before actual use. It would similarly be possible for the user to have to combine portions of the reagent before use or undergo similar manipulations before the reagent can actually be used.

The development of the preservative system described above was undertaken for a product used in the critical care area of clinical chemistry, and a sample formulation utilizing this preservative is shown below. However, it is expected that, because of the generally similar nature of ingredients used in clinical chemistry and related products, this synergistic preservative system is usable for many products that are water based or which are diluted or dissolved with water prior to or during use. Furthermore, since Dantogard is an example of a formaldehyde donor-type preservative and Kathon CG is an example of a non-formaldehyde donor-type preservative, other preservatives in these families also show synergism when mixed together. The formaldehyde donor-type classes that were found to be components of synergistic systems were the N-methylol compounds and the oxazolidines. The non-formaldehyde donor-type preservatives found to be components of synergistic systems were the isothiazolinone-type and the substituted acetals.

The following are provided to exemplify the application of the above development but are not intended to limit its usefulness.

EXAMPLE 1

FORMULATION OF PRODUCTS CONTAINING SYNERGISTIC PRESERVATIVE SYSTEM

| Component | Prod. A | Prod. B |
| --- | --- | --- |
| NaCl | 120.0 | 75.0 |
| KCl | 5.0 | 10.0 |
| Ca(OAc)$_2$ | 1.0 | 3.0 |
| NaOAc | | 30.0 |
| Mg(OAc)$_2$ | | 7.0 |
| HEPES | 25.0 | |
| NaHEPES | 30.0 | |
| MOPS | | 15.0 |
| NaMOPS | | 10.0 |
| Brij-35 (g/L) | 0.3 | 0.3 |
| Kathon CG/II (% w/w) | | 0.05 |
| Kathon CG (% w/w) | 0.05 | |
| Dantogard (% w/w) | 0.3 | 0.3 |

NOTES:
Concentrations are in mmol/L, except where otherwise noted.
OAc is Acetate.
HEPES is 4-(2-hydroxyethyl)-1-piperazine-ethanesulfonic acid.
NaHEPES is its sodium salt.
MOPS is 4-morpholinepropanesulfonic acid.
NaMOPS is its sodium salt.
Brij-35 is polyoxyethylene(23) lauryl ether.
Kathon CG is a solution of 1% of 5-chloro-2-methyl-4-isothiazolin-3-one and 0.35% of 2-methyl-4-isothiazolin-3-one.
Dantogard is a 39.5% solution of dimethylol-5,5-dimethylhydantoin.

To prepare the above products, the reagents are simply mixed with water and adjusted to the desired pH value. (Optimum pH's are in the neutral range.)

EXAMPLE 2

PRESERVATIVE EFFICACY/SYNERGY STUDY

The following studies were undertaken to investigate the possible synergy in microbicide activity. The general techniques of Kull et al were used.

In all tests, one formulation was used as the "base" formula, and various preservative concentrations were added to determine antimicrobial efficacy. The end point was taken as the Minimum Biocidal Concentration (MBC) at 24 hours after innoculation. To evaluate microbicide activity, the solutions were placed in microtiter plates, which were then innoculated with the given microorganism. After 24 hours, the solutions were plated onto media and incubated at 32° C. After 48 hours, the plates were read. "No growth" was interpreted as an indicator of effectiveness for the organism being evaluated.

The microorganisms used in the testing were DMO, DRO, KMO, KTO (all of which are defined above) and 9027, which is *Pseudomonas aeruginosa* 9027 obtained from ATCC.

TABLE A

| COMPOSITIONS TESTED | | |
| --- | --- | --- |
| Composition #* | Concentration KCG | Concentration DANT |
| 1 | 0 | 0 |
| 2 | 90 | — |
| 3 | — | 1600 |
| 4 | 22.5 | 50 |
| 5 | 2.82 | 400 |
| 6 | 2.82 | 50 |

| ANTIMICROBIAL RESULTS AND SI WHERE APPLICABLE) | | |
| --- | --- | --- |
| Composition #* | DRO | KTO |
| 1 | + | + |
| 2 | − | − |
| 3 | − | ± |
| 4 | −(.28) | −(.28) |
| 5 | −(.28) | −(.28) |
| 6 | ± | −(.06) |

NOTES:
KCG = Kathon CG
DANT = Dantogard
Concentration in ppm a.i. (active ingredient)
− = No growth
+ = Noticeable growth
± = Slight growth
*Compositions 7–9 not reported?

We concluded that Composition #'s 4, 5 and 6 show synergy against the microorganisms tested.

EXAMPLE 3

Additional tests were run using other preservatives, namely Kathon LM, an isothiazolinone type preservative, and Oxaban E, a formaldehyde donor-type preservative, by themselves and in various combinations with the above preservatives. Where more than two preservatives were tested, the method of Kull was appropriately modified:

$$(Qa/QA)+(Qb/QB)+(Qc/QC)+ \ldots = \text{Synergy Index (SI)}$$

TABLE B

| COMPOSITIONS TESTED | | | | |
| --- | --- | --- | --- | --- |
| Comp. # | Conc. KCG | Conc. DANT | Conc. KLM | Conc. OXE |
| 10 | — | — | — | — |
| 11 | 90 | — | — | — |
| 12 | — | 1600 | — | — |
| 13 | — | — | 200 | — |
| 14 | — | — | — | 3000 |
| 15 | — | — | 25 | 187.5 |
| 16 | — | — | 12.5 | 375 |
| 17 | 3.75 | 66.7 | 33.3 | — |
| 18 | 3.75 | 66.7 | 4.2 | — |
| 19 | 3.75 | — | 8.3 | 250 |
| 20 | 1.87 | — | 4.2 | 62.5 |
| 21 | 15 | — | 4.2 | 500 |
| 22 | 3.75 | — | 4.2 | 125 |
| 23 | 15 | — | 8.3 | 125 |
| 24 | 15 | — | 4.2 | 125 |

TABLE B-continued

| | | | | |
|---|---|---|---|---|
| 25 | 22.5 | — | 50 | — |
| 26 | 22.5 | — | — | 93.8 |

ANTIMICROBIAL RESULTS AND SI
(WHERE APPLICABLE)

| Comp. # | DRO | KTO | 9027 | DMO | KMO |
|---|---|---|---|---|---|
| 10 | + | + | + | + | + |
| 11 | − | − | − | − | − |
| 12 | − | ± | − | − | − |
| 13 | + | + | + | − | − |
| 14 | ± | − | − | ± | ± |
| 15 | + | ± | −(.31) | −(.31) | −(.31) |
| 16 | + | ± | −(.37) | ± | −(.37) |
| 17 | −(.23) | −(.23) | − | − | − |
| 18 | ± | −(.10) | − | − | − |
| 19 | −(.35) | −(.35) | − | − | − |
| 20 | ± | −(.22) | − | − | − |
| 21 | −(.25) | −(.25) | − | − | − |
| 22 | ± | −(.27) | − | − | − |
| 23 | −(.16) | −(.16) | − | − | − |
| 24 | ± | −(.16) | − | − | − |
| 25* | ± | ± | − | − | − |
| 26 | −(.28) | −(.28) | − | − | − |

NOTES:
KLM = Kathon LM
OXE = Oxaban E
Concentration in ppm a.i. (active ingredient)
*SI ≧ 1.0

We concluded that:

1. Kathon CG with Kathon LM showed no synergy at the concentrations tested (Composition 25).
2. Kathon LM with Oxaban E is ineffective against DRO and 9027 but slightly synergistic against DMO and KMO (Compositions 15 and 16).
3. Kathon CG with Oxaban E is effective against all organisms tested and is synergistic against DRO and KTO (Composition 26).
4. The ternary combination of Kathon CG, Dantogard and Kathon LM is synergistic against DRO and KTO (Compositions 17 and 18), as is also the ternary combination of Kathon CG, Kathon LM and Oxaban E (Compositions 19–24).

EXAMPLE 4

Additional tests were run, using other preservatives, in a solution matrix similar to Example 3, but without any buffering agent. The preservatives used were Kathon CG/II, an isothiazoline type preservative, Bronidox K, an acetal type preservative, and Proxel GXL, an isothiazolinone type preservative, along with Dantogard, a formaldehyde donor preservative.

TABLE C

COMPOSITIONS TESTED

| Comp. # | Conc KCG/II | Conc DANT | Conc BRON K | Conc PROXEL |
|---|---|---|---|---|
| 27 | 75 | | | |
| 28 | 37.5 | | | |
| 29 | 18.7 | | | |
| 30 | 9.4 | | | |
| 31 | 4.7 | | | |
| 32 | | 1600 | | |
| 33 | | 800 | | |
| 34 | | 400 | | |
| 35 | | 200 | | |
| 36 | | 100 | | |
| 37 | | | 200 | |
| 38 | | | 100 | |
| 39 | | | 50 | |
| 40 | | | 25 | |
| 41 | | | 12.5 | |
| 42 | | | | 190 |
| 43 | | | | 95 |
| 44 | | | | 47.5 |
| 45 | | | | 23.7 |
| 46 | | | | 11.9 |
| 47 | | 400 | 50 | |
| 48 | | 200 | 50 | |
| 49 | | 100 | 50 | |
| 50 | | 400 | | 23.7 |
| 51 | | 100 | | 47.5 |
| 52 | 12.5 | 267 | 4.2 | |
| 53 | 6.2 | 133 | 4.2 | |
| 54 | 3.1 | 67 | 16.7 | |
| 55 | 3.1 | 267 | | 31.7 |
| 56 | 12.5 | 133 | | 15.8 |
| 57 | 3.1 | 133 | | 15.8 |
| 58 | 12.5 | 67 | | 7.9 |
| 59 | 12.5 | 33 | | 4 |

ANTIMICROBIAL RESULTS AND SI
(WHERE APPLICABLE)

| Comp. # | DRO | KTO | 9027 | DMO | KMO |
|---|---|---|---|---|---|
| 27 | − | − | − | − | − |
| 28 | − | − | − | − | − |
| 29 | − | − | − | − | − |
| 30 | − | − | − | ± | + |
| 31 | − | 6 | − | + | + |
| 32 | + | − | − | + | + |
| 33 | + | 1 | − | + | + |
| 34 | + | ± | ± | + | + |
| 35 | + | + | + | + | + |
| 36 | + | + | + | + | + |
| 37 | − | − | − | + | + |
| 38 | − | 8 | − | + | + |
| 39 | 8 | 16 | − | + | + |
| 40 | ± | 30 | − | + | + |
| 41 | + | + | ± | + | + |
| 42 | ± | 18 | − | + | + |
| 43 | + | ± | − | + | + |
| 44 | + | ± | 1 | + | + |
| 45 | + | + | ± | + | + |
| 46 | + | + | − | + | + |
| 47 | ± | −(.50) | − | + | + |
| 48 | ± | −(.37) | − | + | + |
| 49 | ± | −(.31) | − | + | + |
| 50 | + | + | −(.75) | + | + |
| 51 | + | ± | −(.63) | + | + |
| 52 | − | − | − | −(.85) | ± |
| 53 | − | −(.77) | − | 8 | ± |
| 54 | 2 | −(.45) | − | + | + |
| 55 | 20 | −(.66) | − | + | + |
| 56 | − | − | − | −(.83) | ± |
| 57 | − | −(.50) | − | + | + |
| 58 | − | − | − | −(.75) | 4 |
| 59 | − | − | − | −(.70) | 8 |

NOTES:
KCG/II = Kathon CG/II
BRON K = Bronidox

We concluded that:

1. No synergy index can be calculated for the DRO or 9027 in any case where Kathon CG/II was used, since the lowest level of KCG/II alone was effective in this study.
2. The combination of Dantogard and Bronidox is highly synergistic against the KTO (minimum SI=0.31) (composition 49).
3. The combination of Dantogard and Proxel GXL is synergistic against the 9027 organism (minimum SI=0.63) (composition 51).

4. The ternary combination of KCG/II, Dantogard and Bronidox is synergistic against the KTO (minimum SI=0.45) (composition 54), and slightly synergistic against the DMO (SI=0.85) (composition 52).

5. The ternary combination of KCG/II, Dantogard and Proxel is synergistic against the KTO (minimum SI=0.50) (composition 57) and slightly synergistic against the DMO (minimum SI=0.70) (composition 59).

6. None of the combinations tested show synergy against the KMO.

What is claimed is:

1. A method for killing microorganisms in an aqueous composition which comprises adding thereto a synergistic mixture of a first component, which is 1,3-bis-(hydroxymethyl)-5,5-dimethyl-2,4-imidazolidinedione, and a second component, which is a mixture of 5-chloro-2-methyl-4-isothiazolin-3-one and 2-methyl-4-isothiazolin-3-one, wherein the ratio of the first component to the second component ranges from about 2:1 to about 1200:1.

2. A method for inhibiting the growth of microorganisms in an aqueous composition, said method comprising providing in said composition a synergistic mixture of a first component, which is 1,3-bis-(hydroxymethyl)-5,5-dimethyl-2,4-imidazolidinedione, and a second component, which is a mixture of 5-chloro-2-methyl-4-isothiazolin-3-one and 2-methyl-4-isothiazolin-3-one, to form a final composition, said first and second components being present in said final composition in the weight ratio of from about 2:1 to about 1200:1.

3. A method of claim 2 wherein the concentration of the first component is between 50 and 1600 ppm of active ingredient and the concentration of the second component is between 1 and 20 ppm of total active ingredients.

4. A method of claim 2 in which said first component is Dantogard and said second component is Kathon CG.

5. An antimicrobial composition for a clinical chemistry reagent, comprising a synergistic mixture of a first component, which is 1,3-bis-(hydroxymethyl)-5,5-dimethyl-2,4-imidazolidinedione, and a second component, which is a mixture of 5-chloro-2-methyl-4-isothiazolin-3-one and 2-methyl-4-isothiazolin-3-one, wherein the ratio of the first component to the second component ranges from about 2:1 to about 1200:1.

6. A method for inhibiting the growth of microorganisms in an existing aqueous composition which comprises adding thereto a synergistic mixture of a first component, which is 1,3-bis-(hydroxymethyl)-5,5-dimethyl-2,4-imidazolidinedione, and a second component, which is a mixture of 5-chloro-2-methyl-4-isothiazolin-3-one and 2-methyl-4-isothiazolin-3-one, wherein the ratio of the first component to the second component ranges from about 2:1 to about 1200:1.

7. An antimicrobial composition of claim 5 wherein the concentration of the first component is between 50 and 1600 ppm of active ingredient and the concentration of the second component is between 1 and 20 ppm of total active ingredients.

8. A method of claim 6 wherein the concentration of the first component is between 50 and 1600 ppm of active ingredient and the concentration of the second component is between 1 and 20 ppm of total active ingredients.

9. A method of claim 1 wherein the concentration of the first component is between 50 and 1600 ppm of active ingredient and the concentration of the second component is between 1 and 20 ppm of total active ingredients.

* * * * *